United States Patent [19]
Hendriks et al.

[11] Patent Number: 5,866,113
[45] Date of Patent: Feb. 2, 1999

[54] MEDICAL DEVICE WITH BIOMOLECULE-COATED SURFACE GRAFT MATRIX

[75] Inventors: Marc Hendriks, Hoensbroek; Michel Verhoeven, Maastricht; Linda L. Cahalan; Patrick T. Cahalan, both of Galeen; Benedicte Fouache, Maastricht, all of Netherlands

[73] Assignee: Medtronic, Inc., Minneapolis, Minn.

[21] Appl. No.: 813,470

[22] Filed: Mar. 7, 1997

Related U.S. Application Data

[62] Division of Ser. No. 656,614, May 31, 1996.
[51] Int. Cl.$^6$ ........................ A61K 31/765; A61K 31/78; A61K 27/00; C08L 33/02
[52] U.S. Cl. .................................... 424/78.17; 424/78.18; 424/486; 424/487; 530/815; 530/816; 525/78; 427/2.24; 427/2.25; 427/2.28; 427/2.3
[58] Field of Search ................................ 424/484, 78.17, 424/78.18, 486–487; 530/815–816; 525/64, 78, 937; 427/2.24, 2.25, 2.28, 2.3

[56] References Cited

U.S. PATENT DOCUMENTS

| | | | |
|---|---|---|---|
| 5,229,172 | 7/1993 | Cahalan et al. | 427/536 |
| 5,308,641 | 5/1994 | Cahalan et al. | 427/2 |
| 5,344,455 | 9/1994 | Keogh et al. | 623/11 |
| 5,350,800 | 9/1994 | Verhoeven et al. | 525/54.2 |
| 5,415,938 | 5/1995 | Cahalan et al. | 428/409 |

OTHER PUBLICATIONS

M. Akita et al., "Cell shape and arrangement of cultured aortic smooth muscle cells grown on collagen gels", *Cell Tissue Res.*, 274, 91–95 (1993).

A. Azeez et al., "In Vitro Monocyte Adhesion and Activation on Modified FEP Copolymer Surfaces", *J. Appl. Polym. Sci.*, 58, 1741–1749 (1995).
F. Berthod et al., "Collagen synthesis by fibroblasts cultured within a collagen sponge", *Biomaterials*, 14, 749–754 (1993).
Y. Kinoshita et al., "Soft tissue reaction to collagen–immobilized porous polyethylene: subcutaneous implantation in rats for 20 wk", *Biomaterials*, 14, 209–215 (1993).
T. Okada et al., "Tissue reactions to subcutaneously implanted, surface–modified silicones", *J. Biomed. Mat. Res.*, 27, 1509–1518 (1993).
T. Okada et al., "Surface Modification of Silicone for Tissue Adhesion", *Biomaterials and Clinical Applications*, Proceedings of the Sixth European Conference on Biomaterials, Bologna, Italy (Sep. 14–17, 1986), pp. 465–470.
H. Park et al., "Mechanisms of Mucoadhesion of Poly-(acrylic Acid) Hydrogels", *Pharm. Res.*, 4, 457–464 (1987).
A.E. Potter Jr. et al., "The Vapor Phase Association of Acetic–$d_3$ Acid–d", *J. Phys. Chem.*, 59, 250–254 (1955).
Y. Shimizu et al., "Studies on Composites of Collagen and a Synthetic Polymer", *Biomat. Med., Dev., Art. Org.*, 6, 375–391 (1978).
Y. Shimizu et al., "Studies on Copolymers of Collagen and a Synthetic Polymer", *Biomat. Med., Dev., Art. Org.*, 5, 49–66 (1977).

*Primary Examiner*—Edward J. Webman
*Attorney, Agent, or Firm*—Daniel W. Latham; Harold R. Patton

[57] ABSTRACT

A medical device having a surface graft matrix comprising carboxyl-functional groups located on the device, the surface graft matrix comprising an outer portion; and one or more biomolecules covalently coupled to the surface graft matrix, wherein a majority of the biomolecules are located in the outer portion of the surface graft matrix. The surface graft matrix can also be loaded with a pharmaceutical agent.

20 Claims, 3 Drawing Sheets

MEDICAL DEVICE WITH BIOMOLECULE-COATED SURFACE GRAFT MATRIX

This is a divisional of copending application Ser. No. 08/656,614 filed on May 31, 1996.

FIELD OF THE INVENTION

The present invention relates to the field of medical devices. More particularly, the present invention relates to medical devices incorporating a biomolecule-coated surface graft matrix and methods of manufacturing the same.

BACKGROUND OF THE INVENTION

Infection has become the most serious complication associated with the application of implantable medical devices. Treatment of these infections is difficult and most often necessitates removal of the implanted device. Technological refinements in materials and design and increasing surgical experience has lowered the incidence of infectious complications; however, infection remains a continuing cause of morbidity and mortality.

Approaches to reduce device-related infections initially were focused on improvements of the surgical technique, including modification of the operating room area and the use of prophylactic antibiotics at the time of surgery. Despite the introduction of these meticulous aseptic measures the occurrence of device-related infections could not be completely eliminated.

An alternative approach is to focus on the implant itself, and consequently on modification of the device to enhance infection-resistance by providing surfaces on the device that promote appropriate integration of the surrounding tissue(s) with the device surface. The underlying concept is that when rapid colonization and integration of the device surface with tissue cells is encouraged, the implant surface will be protected from bacterial colonization.

One method of promoting tissue integration is through the use of collagen immobilized on the surface of the device because collagen materials promote a favorable tissue response. They provide a more physiological, isotropic environment that has been shown to promote the organization of different cell types into three-dimensional tissue-like structure. See, for example, Akita et al., *Cell Tissue Res.*, 274, 91–95 (1993); and Berthod et al., *Biomaterials*, 14, 749–754 (1993). Implant studies have demonstrated that collagen-immobilization promotes favorable integration of tissue(s) with the implanted material. See, for example, Shimizu et al., *Biomat., Med. Dev., Artif. Org.*, 6, 375–391 (1978); Kinoshita et al., *Biomaterials*, 14, 209–215 (1993); and Okada et al., *J. Biomed. Mater. Res.*, 27, 1509–1518 (1993).

One method of coating synthetic polymers with collagen involves a physical deposition of collagen, such that a laminar material results, as disclosed by Shimizu et al., *Biomat., Med. Dev., Artif. Org.*, 5, 49–66 (1977). One drawback to this method is that the collagen materials are prone to delamination in a moisture-abundant environment such as that typically experienced by implanted medical devices.

Another method of providing a collagen-coated device involves covalently coupling collagen to a synthetic polymer substrate, as disclosed by Okada et al., *Biomaterials and Clinical Applications*, Elsevier Science Publishers B.V., Amsterdam, The Netherlands, pp. 465–470, 1987. The method includes graft copolymerization of acrylic acid, after which collagen is covalently coupled to the grafted poly (acrylic acid) chains, resulting in a blend-like matrix of collagen and poly(acrylic acid) chains. This construction is schematically depicted in FIG. 1, where the poly(acrylic acid) chains 12 are grafted to the surface 10 of a device. Collagen 14 is contained within the matrix formed by the chains 12. Thus, the collagen is not located primarily at the surface. Thus, biological activity may be reduced as proper expression and accessibility are hampered.

SUMMARY OF THE INVENTION

The present invention provides a medical device. The medical device comprises: a) a surface graft matrix comprising carboxyl-functional groups located on the device, the surface graft matrix comprising an outer portion; and b) one or more biomolecules covalently coupled to the surface graft matrix, wherein a majority of the biomolecules are located in the outer portion of the surface graft matrix.

Also provided is a medical device comprising: a) a surface graft matrix comprising carboxyl-functional groups located on the device, the surface graft matrix comprising an outer portion; b) one or more linker molecules covalently coupled to the surface graft matrix, wherein a majority of the linker molecules are located in the outer portion of the surface graft matrix; and c) one or more biomolecules covalently coupled to the linker molecules.

The present invention also provides a method of modifying the surface of a medical device. The method comprises: (a) forming a surface graft matrix comprising carboxyl-functional groups on the surface of a medical device; (b) treating the surface graft matrix with an aqueous solution having a pH that is less than the pKa of the surface graft matrix; and (c) covalently coupling one or more biomolecules to the surface graft matrix in an aqueous solution having a pH that is less than the pKa of the surface graft matrix, wherein a majority of the biomolecules are located in the outer portion of the surface graft matrix.

Also provided is a method of modifying the surface of a medical device comprising: (a) forming a surface graft matrix comprising carboxyl-functional groups on the surface of a medical device; (b) treating the surface graft matrix with an aqueous solution having a pH that is less than the pKa of the surface graft matrix; (c) covalently coupling one or more linker molecules to the surface graft matrix in an aqueous solution having a pH that is less than the pKa of the surface graft matrix, wherein a majority of the linker molecules are located in the outer portion of the surface graft matrix; and (d) covalently coupling one or more biomolecules to the linker molecules.

The present invention also provides a method of delivering a pharmaceutical agent. The method comprises contacting a body with a medical device comprising a surface graft matrix comprising carboxyl-functional groups located on the device, the surface graft matrix comprising an outer portion in which a majority of one or more biomolecules are coupled, wherein the pharmaceutical agent is located within the surface graft matrix when the device is initially contacted with the body.

DETAILED DESCRIPTION OF THE INVENTION

Figure 1:
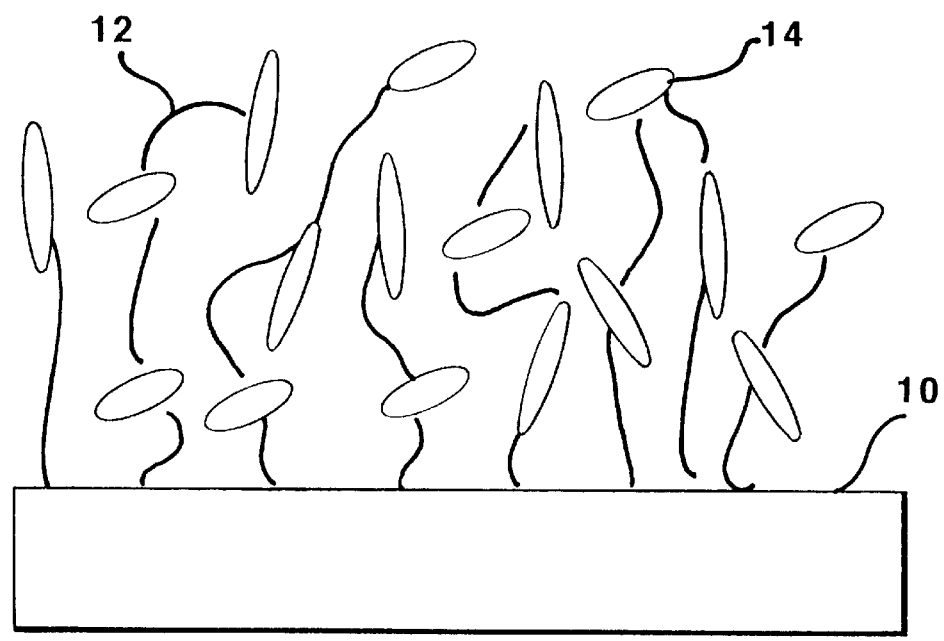
FIG. 1 is a schematic cross-sectional diagram of a prior art surface graft matrix incorporating collagen.

The present invention provides methods of covalently coupling a majority of one or more biomolecules in the outer portion of a surface graft matrix on a medical device. The surface graft matrix is preferably formed by surface grafting carboxyl-functional monomers, optionally in combination with vinyl monomers having no carboxyl functionality (COOH). For example, the surface graft matrix can result from the surface grafting of acrylic acid and acrylamide monomers, as disclosed in U.S. patent application Ser. No. 08/553,206, filed Nov. 7, 1995, entitled "Intramuscular Stimulation Lead With Enhanced Infection Resistance." As a result of the carboxyl functionality, the surface graft matrix typically has an anionic character.

In one method according to the present invention, a surface graft matrix that exhibits reduced permeability to medium-sized to large molecules is formed on the surface of a medical device, thereby providing the ability to isolate a majority of the subsequently coupled biomolecules to the outer portion of the surface graft matrix. The permeability of the surface graft matrix is reduced by treatment of the surface graft matrix at reduced pH levels, preferably where the pH of the solution is less than the pKa of the surface graft matrix. By carrying out biomolecule coupling reactions in solutions in which the pH is less than the pKa of the surface graft matrix, the relative impermeability of the surface graft matrix is maintained, restricting a majority of the biomolecules to the outer portion of the surface graft matrix. That restriction results in a "sheath" of biomolecule(s) over the surface graft matrix.

In another method according to the present invention, the surface graft matrix can be loaded with a pharmaceutical agent after the biomolecules are in place in the outer portion of the surface graft matrix. Preferably, this loading occurs as a result of ionic interaction of the surface graft matrix with the pharmaceutical agent.

In another method according to the present invention, a surface graft matrix exhibiting reduced permeability to medium-sized to large molecules is formed on the surface of a medical device. The permeability of the graft matrix is reduced by treatment of the surface graft matrix at reduced pH levels, preferably where the pH of the solution is less than the pKa of the surface graft matrix. By carrying out subsequent coupling reactions of one or more linker molecules (which may be biomolecules, referred to herein as intermediate biomolecules) in solutions with a pH less than the pKa of the surface graft matrix, the relative impermeability of the graft matrix is maintained, restricting a majority of the linker molecules to the outer portion of the graft matrix. That restriction results in a "sheath" of linker molecules (e.g., intermediate biomolecules) in the outer portion of the surface graft matrix. The linker molecules (e.g., intermediate biomolecules) can then be used to covalently couple a majority of second biomolecules (referred to herein as primary biomolecules) in the outer portion of the surface graft matrix. This second coupling step is also preferably performed in solutions having pH values less than the pKa of the underlying surface graft matrix, thereby maintaining its relative impermeability to the biomolecules located in the outer portion of the surface graft matrix.

As used herein, the term "medical device" may be defined as a device that has surfaces that contact tissue, blood, or other bodily fluids in the course of their operation, which fluids are later used in patients. This can include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can also include nerve electrodes, muscle electrodes, implantable pulse generators, implantable drug pumps, and defibrillators.

As used herein, the term "biomolecule" includes any biocompatible and/or biologically active molecule (i.e., "primary biomolecule") or an intermediate biomolecule (linker molecule) to which one or more primary biomolecules can be coupled. Unless otherwise indicated, the term "biomolecule" as used herein will be understood to include both primary and intermediate biomolecules.

An example of a biomolecule is collagen, a biocompatible molecule that exists in many types. Types of biomolecules that can be coupled to the surface graft matrix in accordance with the present invention include, but are not limited to, antithrombotic agents, antibacterial agents, anti-inflammatory agents, growth factors, cytokines, naturally occurring or synthetically prepared proteins, peptides, amino acids, and mixtures thereof. Specific examples of biomolecules that can be coupled to the surface graft matrix include, but are not limited to, albumin, fibrinogen, laminin, vitronectin, fibronectin, RGD-containing peptides, heparin, heparin sulfate, fibroblast growth factors (FGF), insulin-like growth factor, nerve growth factor, interferons (IFN), tumor necrosis factors (TNF), interleukins, gelatin, elastin, fibrin, von Willebrand factor, dermatan sulfate, hyaluronic acid, dextran sulfate, and mixtures thereof. These biomolecules may be neutral or charged at the conditions employed during covalent coupling. They may be coupled to the surface graft matrix directly (i.e., through the carboxyl groups), or through well-known coupling chemistries, such as, for example, esterification, amidation, and acylation. These biomolecules are typically the primary biomolecules, although certain of them can be used as the intermediate biomolecules. It will be understood that the outer sheath of biomolecules typically includes a plurality of biomolecules, although it could include polymerized biomolecules that technically form one macromolecule.

The use of linker molecules, which may or may not be biomolecules, in connection with the present invention typically involves covalently coupling a majority of the linker molecules in the outer portion of the surface graft matrix. After covalent coupling to the surface graft matrix, the linker molecules can provide the surface graft matrix with a number of functionally active groups that can be used to covalently couple one or more primary biomolecules. The linker molecules may be coupled to the surface graft matrix directly (i.e., through the carboxyl groups), or through well-known coupling chemistries, such as, for example, esterification, amidation, and acylation. Preferably, the linker molecule is at least a di-or tri-amine functional compound that is coupled to the surface graft matrix through the direct formation of amide bonds, and provides amine-functional groups that are available for reaction with the primary biomolecule. More preferably, the linker molecule is a polyamine functional polymer such as polyethyleneimine (PEI) or polyallylamine (PALLA). Mixtures of these polymers can also be used. These molecules contain a plurality of pendant amine-functional groups that can be used to surface-immobilize one or more primary biomolecules.

Figure 2:
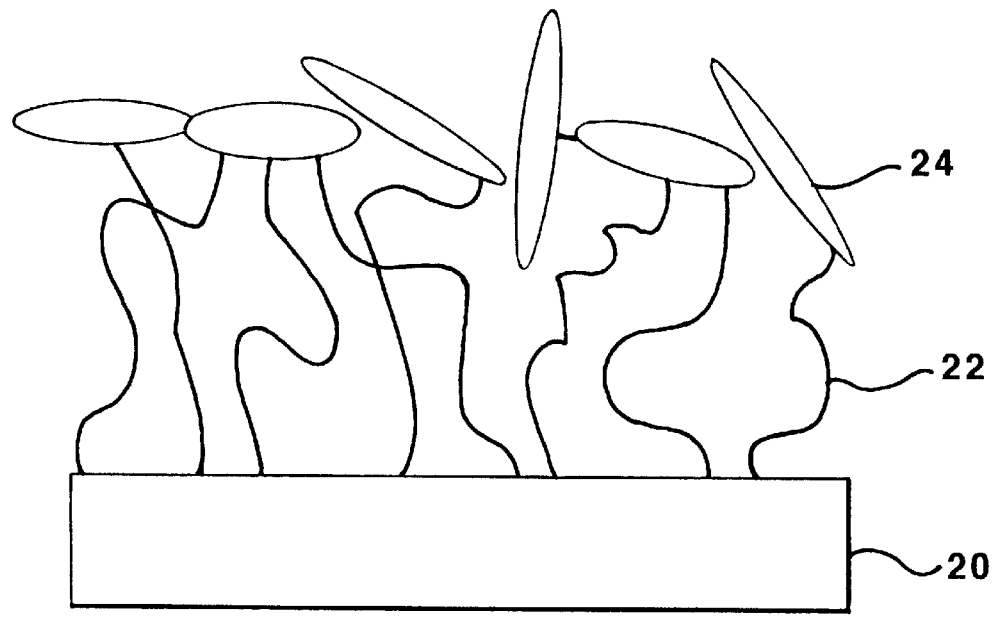
FIG. 2 is a schematic cross-sectional diagram of a surface graft matrix coated with a biomolecule sheath.

FIG. 2 is a schematic cross-sectional view of a portion of the surface of a medical device 20, depicting that the biomolecules 24 are covalently coupled to a surface graft matrix 22 in a manner such that a majority of the biomolecules 24 are located or immobilized in the outer portion of the surface graft matrix 22 located on the medical device 20. The immobilization of the biomolecules 24 as depicted in FIG. 2 differs from the prior art depicted in FIG. 1 in that a majority of the biomolecules 24 are located on or near the outer surface of the surface graft matrix 22, not generally dispersed throughout the structure of the matrix as depicted in FIG. 1. This surface isolation of a majority of the biomolecules is advantageous because it allows a less disturbed expression of the biomolecules, so that biological activity is retained at a significantly higher level.

The depth of the outer portion of the surface graft matrix in which a majority of the biomolecules are immobilized is primarily dependent on the type of biomolecule immobilized and the reaction conditions employed. Typically, a majority of the biomolecules will be immobilized in the surface graft matrix within a depth of about 10 nm or less. For example, if collagen is the biomolecule immobilized in the outer portion of the surface graft matrix, the depth at which a majority of the collagen molecules are immobilized is about 7 nm or less.

The immobilization approach of the present invention may prohibit movement of the coupled biomolecules into the graft matrix. This will especially be the case with immobilization of anionic biomolecules, such as the anticoagulant heparin which will be repelled by the underlying anionic surface graft matrix.

As discussed above, after the covalent coupling of a majority of the biomolecules in the outer portion of the surface graft matrix, the matrix can be loaded with a pharmaceutical agent for subsequent release to effect a desired response in the patient. By immobilizing the majority of the biomolecules in the outer portion of the surface graft matrix, the pharmaceutical agent capacity of the matrix can be increased as compared to those surface graft matrix materials that allow complete penetration of biomolecules. This provides yet another advantage of the present invention.

Pharmaceutical agents that can be used in connection with the present invention include, but are not limited to, antimicrobial agents, antibacterial agents, anticoagulant agents, antithrombotic agents, platelet agents, and anti-inflammatory agents. Other useful pharmaceutical agents can include, but are not limited to, dyes which act as biological ligands, steroids, enzymes, catalysts, hormones, growth factors, drugs, vitamins, antibodies, antigens, nucleic acids, peptides, DNA & RNA segments, and mixtures thereof. For most effective incorporation into the surface graft matrix, these pharmaceutical agents are hydrophilic, positively charged compounds.

Figure 3:
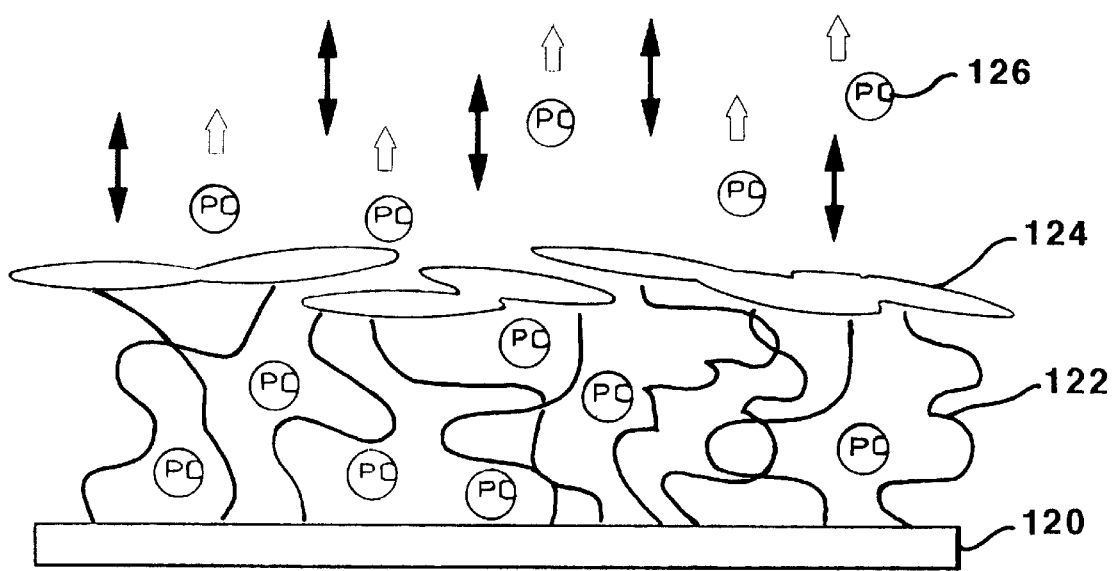
FIG. 3 is a schematic cross-sectional diagram of a surface graft matrix coated with a biomolecule sheath, where the surface graft matrix is loaded with a pharmaceutical agent.

Referring now to FIG. 3, in a medical device 120 incorporating a biomolecule 124 on a surface graft matrix 122 loaded with a desired pharmaceutical agent 126, duplicate biological activities can be provided to improve the in vivo performance of the medical device. The biomolecules 124 can be, for example, collagen which will interact with the surrounding tissue to provide a favorable tissue integration. By release of the pharmaceutical agent 126, specific desired body mechanisms may be activated, or, in the case of antimicrobials, a protective mode of action is exhibited during the initial vulnerable period before the medical device/tissue interface is stabilized and when random colonization by bacteria might occur. As a result, the surface exhibits "bi-biofunctional" characteristics, i.e., two biofunctional activities including: a) promoting rapid tissue integration into the surface of the device, and b) releasing a pharmaceutical agent, such as an antimicrobial agent to reduce the risk of infection around an implanted device.

Processes according to the present invention typically begin with the formation of a surface graft matrix on the surface of a medical device. The surface grafting method involves the covalent surface grafting of a polymer, preferably water soluble polymer, based on carboxyl-functional monomers, including, but not limited to, acrylic acid, methacrylic acid, itaconic acid, trans-cinnamic acid, crotonic acid, linoleic acid, linolenic acid, maleic acid, sorbic acid, and mixtures thereof onto a substrate material. The carboxyl-functional surface graft matrix also may be obtained through chemical modification of non-carboxyl-functional monomers. For example, basic hydrolysis of a poly(acrylamide) surface will introduce carboxyl-functional moieties, similar to what occurs when acrylic acid is copolymerized with acrylamide. However the surface graft matrix is prepared, as long as it has carboxyl-functional groups (COOH) it can be used to attach biomolecules as described herein.

Surface grafting is preferably initiated by ceric ion methods as discussed U.S. Pat. Nos. 5,229,172 and/or 5,344,455. While ceric ion initiation is a preferred method to graft monomers to substrate surfaces, other grafting techniques may be used as well. Known examples of other initiation methods include corona discharge, UV irradiation, ozonization and ionizing radiation (e.g., $^{60}$Co, X-rays, high energy electrons, plasma gas discharge, etc.).

The substrates that can be modified by the method of the present invention include metals such as titanium/titanium alloys, TiNi (shape memory/super elastic), aluminum oxide, platinum/platinum alloys, stainless steels, MP35N, elgiloy, haynes 25, stellite, pyrolytic carbon, silver or glassy carbon; polymers such as polyamides, polycarbonates, polyethers, polyesters, polyolefins including polyethylenes or polypropylenes, polystyrenes, polyurethanes, polyvinyl chlorides, polyvinylpyrrolidones, silicone elastomers, fluoropolymers, polyacrylates, polyisoprenes, polytetrafluoroethylenes, and rubber; minerals or ceramics such as hydroxapatite; human or animal protein or tissue such as bone, skin, teeth, collagen, laminin, elastin or fibrin; organic materials such as wood, cellulose, or compressed carbon; and other materials such as glass, or the like. Substrates made using these materials can be coated or uncoated, and derivatized (e.g., modified to include reactive functional groups) or underivatized. Preferably, the substrate is polyurethane, to which the carboxyl-functional surface graft matrix can be directly coupled without any preactivation of the substrate surface.

Surface grafting can be used to modify substrates of any shape or form including tubular, sheet, rod and articles of proper shape. Preferably, the substrate is a biomaterial for use in a number of medical devices such as vascular grafts, aortic grafts, arterial, venous, or vascular tubing, vascular stents, dialysis membranes, tubing, or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind.

A polymer surface graft of acrylic acid is one preferred embodiment to be used for subsequent covalent coupling of one or more biomolecules to enclose the surface graft matrix. The surface graft matrix is preferably formed by surface grafting of the monomers acrylic acid and acrylamide in ratios that allow for later manipulation of the graft matrix. Typically, sufficient acrylic acid (or other carboxylic-functional monomer) should be present so as not to interfere with the mechanism of reducing the permeability of the surface graft matrix to provide for immobilization of a majority of the biomolecules in the outer portion of the surface graft matrix. Preferably, acrylic acid is used to prepare the surface graft matrix in an amount of about 20–100 wt-%, based on the total weight of the monomers used to prepare the surface graft matrix. More preferably, acrylic acid is used in an amount of about 50–90 wt-%, and most preferably, in an amount of about 65–75 wt-%. These weight percentages are also applicable to other carboxyl-functional monomers.

Incorporation of other vinyl-functional monomers that do not include carboxyl groups (COOH) into the surface graft is possible, but is limited to the extent that they interfere with the mechanism of reducing the permeability of the surface graft matrix to provide for isolation of a majority of the biomolecules in the outer portion of the surface graft matrix. Various vinyl-functional monomers can be incorporated to form a copolymer surface graft, such as acrylamide (Aam), N-(3-aminopropyl) methacrylamide (APMA), 2-hydroxyethyl methacrylate (HEMA), and 2-acrylamido-2-methylpropane sulfonic acid (AMPS). Acrylamide is the most preferred monomeric compound to be incorporated in addition to acrylic acid monomer as the structure and molecular weight of acrylamide are close to those of acrylic acid.

After covalent coupling of the surface graft matrix to the substrate surface (which may or may not be carried out in acidic media), as exemplified in the examples below, a low pH immersion process is used to produce the surface graft matrix with the desired impermeability to provide for immobilization of a majority of the biomolecules in the outer portion of the surface graft matrix. By immersing the surface graft matrix in a low pH solution, the formation of carboxylic acid dimers and intra-polymer crosslinking in the surface graft matrix is provided. The bond strength of acetic acid dimers is approximately equal to 55–60 kJ/mole, as disclosed by Potter, Jr., et al., *J. Phys. Chem.*, 59, 250–254 (1955). This indicates that intrapolymer crosslinking within a poly(carboxylic acid) graft matrix will be of significant strength. The formation of intrapolymer crosslinks is characterized by an obvious sticky feel of the surface grafted material. This sticky feel is generally indicative of the cohesive forces of the surface graft matrix. The intrapolymer crosslinking reduces the permeability/accessibility of medium-sized to large, even polycationic, compounds into the surface graft matrix.

A subsequent process of covalently coupling a majority of biomolecules in the outer portion of the surface graft matrix is also carried out at a pH that is less than the pKa of the surface graft matrix. This results in immobilization of the biomolecules such that a surface layer of primarily biomolecules, i.e., a sheath, is formed that substantially encloses the surface graft matrix. This additionally allows for more complete loading of the surface graft matrix with a pharmaceutical agent for subsequent release in vivo. Although it is preferred that the immersion process and the biomolecule coupling process be carried out sequentially, they could be carried out simultaneously.

The pKa value of the surface graft matrix can be determined through FT-IR analysis, according to the method of Azeez et al., *J. Appl. Polym. Sci.*, 58, 1741–1749 (1995). Using this method, the pKa of a 100% acrylic acid graft matrix is 6.3, which is in accordance with the findings of 4.9–6.7 disclosed by Park et al., *Pharm. Res.*, 4, 457–464 (1987) on acrylic acid/acrylamide copolymer hydrogels. The pKa values are generally dependent on the ionic strength of the environment and the fraction of acrylic acid in the copolymer. Typically, an increase in ionic strength decreases the pKa, whereas an increase in acrylic acid fraction increases the pKa.

Typically, the pH of the solutions in which the surface graft matrix is treated to reduce permeability and in which biomolecules are attached are typically no greater than about 5.5. Preferably, the pH is no greater than about 5, and more preferably, no greater than about 4.5. Preferably, the pH is at least about 2, and more preferably, at least about 3. Some specific solution pH values are described in connection with the examples presented below.

Specifically, the methods of the present invention preferably involve surface grafting of carboxyl-functional monomers through a covalent interaction to a substrate at an acidic pH, preferably at a pH of less than about 5.5; washing the substrate with the surface graft matrix thereon in an aqueous solution having a pH greater than the pKa of the surface graft matrix (typically at a neutral pH) to allow for the removal of free monomers, oligomers, or polymers; immersing the substrate with the surface graft matrix thereon in a solution having a pH that is less than the pKa of the surface graft matrix; and covalently coupling a majority of the biomolecules in the outer portion of the surface graft matrix in a solution having a pH that is less than the pKa of the surface graft matrix.

Methods and medical devices according to the present invention will be described in connection with the following non-limiting examples.

EXAMPLES

Materials

Polyurethane (PU) film material was made from 2363-55D PELLETHANE resin (Dow Chemical, Midland, Mich., USA) by Medtronic Promeon (Minneapolis, Minn., USA).

Ceric(IV)ammonium nitrate, nitric acid (65%), sodium phosphate monobasic monohydrate, sodium phosphate dibasic, sodium chloride, and sodium azide were all obtained from Merck-Schuchardt (Darmstadt, Germany). Acrylic acid, MES monohydrate, di-sodium tartrate, N-hydroxysuccimide (NHS), 3-ethyl-1-(diaminopropyl)-carbodiimide (EDC), and sodium hydrogencarbonate, were obtained from Aldrich Chemie (Bornem, Belgium). Acrylamide (99+%; electrophoresis grade) was obtained from Acros Chimica (Geel, Belgium). Collagen (type I; from calf skin), and 2,4,6-trinitrobenzenesulfonic acid (TNBS; 1M in water) were obtained from Fluka (Buchs, Switzerland). Coomassie Blue was obtained from Pierce Europe BV (Oud Beijerland, The Netherlands). Collagenase (EC 3.4.24.3; from Clostridium histolyticum; type IA, 550 units/mg solid), and Tris-HCl were obtained from Sigma Chemie (Bornem, Belgium); di-sodium tetraborate decahydrate from Sigma Chemie (Borneum, Belgium); Toluidine Blue O dye from Sigma Chemie; Ponceau S dye from Sigma Chemie; SDS from Sigma Chemie; and gentamicin sulfate from Sigma Chemie.

Acrylic acid was purified by conventional distillation. All other reagents were of reagent grade or higher and used without further purification.

Phosphate buffered saline (PBS) was prepared from 0.0085M $Na_2HPO_4$, 0.0015M $NaH_2PO_4.H_2O$, and 0.15M NaCl; pH=7.4.

Test Procedures

All Fourier Transform Infrared (FT-IR) analyses discussed herein were carried out on a BioRad Digilab FTS-60 spectrophotometer equipped with a vertical ATR device; a germanium crystal was used as the internal reflection element under a 45° end-face angle.

All samples evaluated by electron microscopy were first sputter-coated with gold (2–4 nm) using an Edwards S150B Sputter Coater. Evaluation of the materials was carried out on a JEOL JSM 6400 Scanning Electron Microscope (SEM) operated at 15 kV.

All X-Ray Photoelectron Spectroscopy Q(PS) was performed at the Center for Surface and Material Analysis (CSMA Ltd., Manchester, UK) using a Fisons (VG) Surface Science Instruments M-Probe XPS instrument, with variation in take-off angle (TOA) and using 200 W monochromatized $AlK_\alpha$ X-rays focused into an elliptical spot size of 400 $\mu m \times 1000$ $\mu m$. Survey scan analysis and high resolution analysis of C 1s, O 1s, and N 1s regions were recorded. All spectra are referenced to the C 1s peak at 285.0 eV binding energy. Composition tables were derived for each surface by peak area measurement followed by the use of Scofield sensitivity factors. High resolution data were subject to linear background subtraction prior to peak synthesis using the instrument software.

Time of Flight Secondary Ion Mass Spectometry (ToF-SIMS) spectra were acquired using a VG IX23S instrument based on the Poschenreider design and equipped with a pulsed liquid metal ion source. A 30 keV $Ga^+$ primary ion beam was used at an incident angle of 38° to the surface normal. The secondary ions were accelerated to 5 keV for the analysis by applying a sample bias. For each sample, both positive and negative secondary ion spectra were collected using a total primary ion dose that did not exceed $2 \times 10^{11}$ ions $cm^{-2}$ for static SIMS, such that the analyzed surfaces were effectively undamaged as a result of the ToFSIMS studies. Field Emission Gun Scanning Electron Microscope (FEG-SEM) tests were carried out on a JEOL JSM 6301-F Field-Emission-Gun SEM operated at 2 kV after the samples were sputter coated with gold (2–4 nm) using an Edwards 5150B Sputter Coater.

Example 1

Preparation of Surface Graft Matrix

Extruded PELLETHANE 55D polyurethane films were ultrasonically cleaned in isopropyl alcohol (IPA) for 15 minutes prior to ceric ion initiated surface grafting. Immediately after the IPA-cleaning samples were dried in a forced air oven at 50°–60° C. for approximately 5 minutes. FT-IR investigation has demonstrated that 15 minutes IPA-treatment is sufficient to remove any surface contamination that originates from processing aides, such as bis-stearamide waxes, that may interfere with the grafting process.

Meanwhile, an aqueous grafting solution was prepared that was composed of 40% by weight acrylic acid monomer concentration (100 wt-% acrylic acid), 6 mM of ceric ammonium nitrate (CAN) and 0.06M nitric acid ($HNO_3$). Prior to grafting, the grafting solution was treated to remove excess air by exposure to reduced pressure (18 mm Hg±5 mm Hg) for a maximum of 2 minutes.

Grafted samples (10×1 cm strips) were prepared by placing the cleaned and dried samples in an appropriate volume (25–30 ml) of the grafting solution. Grafting was allowed to continue for 15–20 minutes at 30° C., while stirring the solution.

Following grafting, the samples were rinsed in deionized (DI) water to stop the grafting process as well as to clean the surface graft matrix formed. Thorough clean-up of the grafted samples was performed in a phosphate buffered saline (PBS) solution, pH=7.4, for 16–18 hours at 50°–60° C.

To induce dimer formation, the 55D PELLETHANE samples that were surface grafted with acrylic acid monomer only were immersed in a 0.1M tartrate solution (di-sodium tartrate), buffered at pH=3.0 (which is significantly below the pKa of the graft matrix, typically about pH 6) for four hours at room temperature.

The formation of carboxylic acid dimers was confirmed with FT-IR spectroscopy. Two peaks are important; the peak that is representative for carboxylic acid in the ionized state [$COO^-$] located at approximately 1560 nm; and the peak that is representative for carboxylic acid in a dimer-configuration located at approximately 1700 nm. The enlarged peak intensity and peak area at approximately 1700 nm by treatment at pH=3.0 (<<pKa) is obvious and indicative for dimer formation.

Surface analysis by means of X-Ray Photoelectron Spectroscopy (XPS) allows for a quantitative elemental analysis of the surface 1.5 to 6 nm top layer. XPS confirmed the difference in chemical state of the carboxylic acid dependent on the pH. In the tables below the results of the XPS analysis of AA-grafted 55D (100 wt-% acrylic acid) are displayed.

TABLE 1

Surface composition (in atom %) according to XPS.

| Sample | carbon | nitrogen | oxygen | sodium |
|---|---|---|---|---|
| AA-grafted 55D (pH > pKa) | 69.2 | 1.5 | 24.7 | 4.6 |
| AA-grafted 55D (pH < pKa) | 71.1 | 0.4 | 28.5 | — |

TABLE 2

Carbon chemical states according to XPS (in %).

| sample | C—C | C—N | C—O | COOX (ionized) | COOH |
|---|---|---|---|---|---|
| AA-grafted 55D (pH > pKa) | 73.2 | — | 9.4 | 14.9 | 2.5 |
| AA-grafted 55D (pH < pKa) | 69.6 | — | 8.3 | 0.7 | 21.4 |

At pH>the carboxylic acid groups are mainly ionized. This is confirmed by the presence of sodium (Table 1) and the prevalence of the COOX chemical state (Table 2). In the ionized state, carboxylic acids will not be capable of forming the dimer, i.e., the group that is essential for physically crosslinking the graft matrix. In contrast, at pH<pKa the carboxylic acid groups are hydrogenated and thus capable of forming that dimer-group. The hydrogenated state is confirmed by the absence of sodium (Table 1) and the prevalence of the COOH chemical state (Table 2).

As discussed, the surface graft matrix can be made impermeable for medium-sized to large (even polycationic) molecules by formation of carboxylic acid dimers to induce physical crosslinking. This was confirmed in an experiment that studied the effect of pH on the amount of the (polycationic) antimicrobial drug gentamicin that could be (ionically) immobilized.

It was observed that a strongly anionic surface graft could be manipulated such that a polycationic compound, such as gentamicin, could be prevented from entering the polymeric matrix of the surface graft. When the pH falls below the pKa of the surface graft matrix the amount of gentamicin that could be immobilized was drastically reduced to become zero in the pH-range from 3 to 4.

Gentamicin stock solutions were prepared that were buffered at different pH values. Typically, the solutions contained 0.01M of the desired buffer agent; the solution pH was adjusted to the desired pH by dropwise addition of either 1N NaOH or 1N HCl. The pH range extended from pH=3 to pH=9. The solutions were prepared as follows:

TABLE 2A

| pH | Preparation |
| --- | --- |
| 3 | 0.01 M di-sodium tartrate dihydrate + 1 N HCl |
| 4 | 0.01 M di-sodium tartrate dihydrate + 1 N HCl |
| 5 | 0.01 M MES monohydrate + 1 N NaOH |
| 6 | 0.01 M MES monohydrate + 1 N NaOH |
| 7 | 0.01 M MES monohydrate + 1 N NaOH |
| 8 | 0.01 M di-sodium tetraborate decahydrate + 1 N HCl |
| 9 | 0.01 M di-sodium tetraborate decahydrate + 1 N HCl |

After immersion of the surface grafted samples in the corresponding buffered solutions without gentamicin, the surface grafted samples were gentamicin loaded and the amount of gentamicin loaded was determined. The difference in the gentamicin content before and after sample immersion was determined and used as a measure for the amount of gentamicin loaded into the samples.

Gentamicin solutions were adjusted to pH=9 by addition of 0.1M borate buffer (0.1M di-sodium tetraborate decahydrate, pH=9.2), after which 25 µl 0.03M aqueous TNBS was added per ml of sample solution. The TNBS derivatization reaction was allowed to proceed for 25–30 minutes at room temperature, after which the absorbance at 415 nm was measured, while 595 nm was used as the reference wavelength (BioRad Model 3550, 96 wells microplate reader, Veenendaal, The Netherlands).

As indicated above, when the pH falls below the pKa of the surface graft matrix, the amount of gentamicin that could be immobilized was drastically reduced to become zero in the pH range from 3 to 4.

Example 2

Covalent Immobilization of Collagen to the Surface Graft Matrix

55D PELLETHANE polyurethane samples were surface grafted with acrylic acid monomer as discussed in Example 1. Subsequently, the surface grafted samples were immersed in a 0.1M tartrate solution (di-sodium tartrate), buffered at pH=3.0 for four hours at room temperature. After a triplicate rinse in DI water, samples were immersed in a buffered solution containing 0.01M EDC and 0.01M NHS. The solution was buffered in the pH range 4.0–4.5 with 0.02M MES (4-morpholineethanesulfonic acid monohydrate, Aldrich) buffer. The carbodiimide activation reaction was allowed to continue for 5 minutes at room temperature.

Immediately after carbodiimide activation of the carboxylic acid groups as discussed in Example 1, the samples were immersed in a buffered solution containing 0.5 mg/ml collagen (type I). The solution was buffered in the pH range 4.0–4.5 with 0.02M MES. The collagen immobilization reaction was continued for at least 20 hours. Subsequently, the collagen-immobilized samples were rinsed in DI water, an aqueous 0.15M NaCl solution in DI water, and DI water again. Samples were dried at ambient conditions by air exposure.

The immobilization of collagen was identified by two separate staining techniques. TNBS-staining confirmed the presence of amine-functional groups. TNBS staining was performed by immersing a 4 mm disc in 1 ml of aqueous 4% by weight $NaHCO_3$. To this solution 1 ml of aqueous 0.5% by weight TNBS was added, after which the reaction was allowed to continue for 2 hours at 40° C. Finally, the sample was extensively rinsed in DI water and allowed to dry. A similar surface grafted disc, but not used for collagen immobilization, was used as the control. The difference in dye uptake was obvious visually. Considering the surface modification chemistry, these groups could only be derived from immobilized collagen.

Coomassie Blue protein dye also was used as a analytical tool to verify the presence of immobilized collagen in the outer portion of the surface graft matrix. Coomassie Blue staining was performed by immersing a 4 mm disc in 1 ml of Coomassie Blue for 30 minutes. Thereafter, the sample was extensively rinsed in DI water and allowed to dry. A similar surface grafted disc, but not used for collagen immobilization, was used as the control. The difference in dye uptake was obvious visually.

Figure 4:
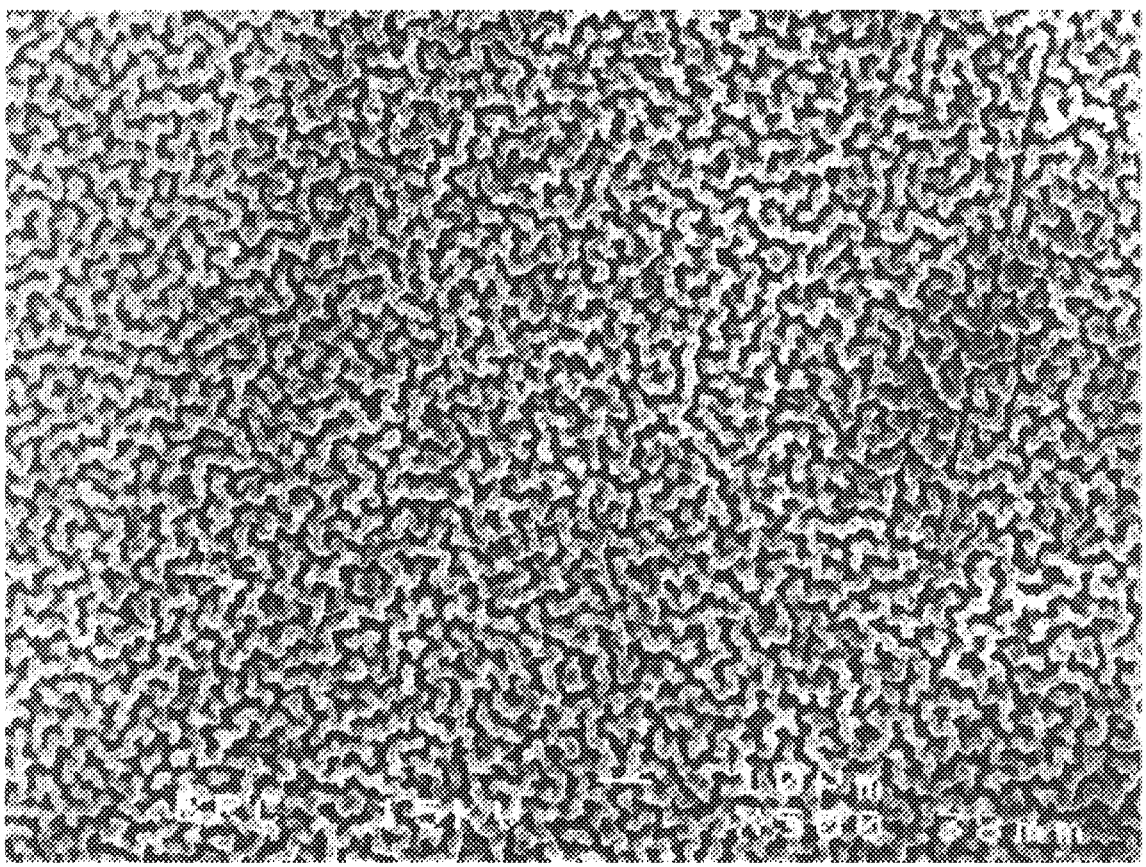
FIG. 4 is a line drawing of the surface appearance of a surface graft matrix coated with collagen in a process according to the present invention.

Additionally, the processed surfaces were examined by FEG-SEM (Field Emission Gun Scanning Electron Microscope) operated at 2 kV; prior to SEM-analysis surfaces were sputter-coated with gold (2–4 nm). The extruded 55D PELLETHANE polyurethane material is a flat material. The acrylic acid grafted material exhibits a permeable matrix-like structure. Subsequent immobilization of collagen seems to have covered this surface matrix with a superimposed surface-layer. The velvet-like appearance of this surface layer is depicted in FIG. 4.

Another analytical technique that was used to confirm the immobilization of collagen was FT-IR spectroscopy. This technique allows for analysis of the top 0.2–1 µm surface layer of processed samples. The FT-IR spectra of collagen raw material, acrylic acid grafted 55D, and collagen-immobilized samples were compared. The spectrum of the collagen-immobilized sample obviously contained features of both the acrylic acid graft and the collagen raw material. Most characteristic was the rise of the collagen-related peaks at approximately 1635 nm and 1660 nm. This confirmed the presence of collagen in the surface top layer.

Surface analysis by means of XPS allows for a quantitative elemental analysis of the surface 1.5–10 nm top layer dependent on the take-off angle (TOA). XPS analysis was performed at a 35° turn-off angle (TOA), which accounts for an approximate 3.0 nm analysis depth. The results of those analyses are presented in Tables 4–7 below.

TABLE 4

Surface composition (in atom %) according to XPS.

| Sample | carbon | oxygen | nitrogen | silicone |
|---|---|---|---|---|
| collagen reference | 69.1 | 17.5 | 11.7 | 1.8 |
| collagen immobilized | 67.9 | 18.9 | 11.8 | 1.4 |

TABLE 5

Carbon chemical states derived from XPS analysis (in %).

| Functional grouping | collagen reference | collagen immobilized |
|---|---|---|
| C—C | 47 | 48 |
| C—N | 23 | 24 |
| C—O | 12 | 11 |
| N—C = O | 13 | 17 |
| O—C = O | 5 | — |

TABLE 6

Oxygen chemical states derived from XPS analysis (in %).

| functional grouping | collagen reference | collagen immobilized |
|---|---|---|
| C = O | 39 | 35 |
| NH—C = O | 38 | 38 |
| C—OH | 17 | 23 |
| $H_2O$ | 6 | 4 |

TABLE 7

Nitrogen chemical states derived from XPS analysis (in %).

| functional grouping | collagen reference | collagen immobilized |
|---|---|---|
| NH—C = O | 70 | 77 |
| —C—NH—C— | 30 | 23 |

As indicated in these results, XPS demonstrated that the collagen was well coupled to the surface graft matrix. The immobilized collagen and collagen reference spectra were very similar, as is displayed in the tables above. This indicates that the surface portion (3 nm) primarily consists of collagen, confirming that surface model depicted in FIG. 2 is correct.

By variation of the take-off angle (TOA) the analysis depth can be varied, and thus more information could be obtained regarding the thickness of the collagen top layer. In the tables below the surface composition as well as the derived chemical functionalities are displayed of collagen-immobilized samples as a function of the analysis depth.

TABLE 8

Surface composition (in atom %) according to XPS.

| TOA | analysis depth (Å) | carbon | nitrogen | oxygen | silicone |
|---|---|---|---|---|---|
| 15° | 15 | 71.4 | 9.1 | 17.3 | 2.2 |
| 35° | 30 | 67.9 | 11.8 | 18.9 | 1.4 |
| 90° | 70 | 64.9 | 13.6 | 20.7 | 0.7 |

Major changes were detected in the 7 nm surface top layer. Both oxygen and nitrogen decrease towards the outer surface, especially from 3 nm depth outwards, whereby the nitrogen concentration drops more steeply.

In the tables below the derived chemical functionalities are displayed. The outermost surface carbon is enriched in C—C, C—H and C—O(H) bonding. The nitrogen is enhance in C—NH—C bonding and the oxygen is enriched in C—OH bonding. This suggests that the collagen amino acids proline and hydroxyproline are likely to be present in increased concentrations at the outermost surface. The latter observation suggests that the collagen-immobilization is accompanied by a reorientation of the collagen molecules.

TABLE 9

Carbon chemical states derived from XPS analysis (in %).

| analysis depth (Å) | C—C/C—H | C—N | C—O | N—C=O | O—C=O |
|---|---|---|---|---|---|
| 15 | 53 | 18 | 14 | 15 | — |
| 30 | 48 | 24 | 11 | 17 | — |
| 70 | 41 | 22 | 16 | 17 | 5 |
| collagen reference | 47 | 23 | 12 | 13 | 5 |

TABLE 10

Oxygen chemical states derived from XPS analysis (in %).

| analysis depth (Å) | C=O | NH—C=O | C—OH | $H_2O$ |
|---|---|---|---|---|
| 15 | 21 | 36 | 36 | 6 |
| 30 | 35 | 38 | 23 | 4 |
| 70 | 38 | 37 | 21 | 4 |
| collagen reference | 39 | 38 | 17 | 6 |

TABLE 11

Nitrogen chemical states derived from XPS analysis (in %).

| analysis depth (Å) | NH—C=O | —C—NH—C— |
|---|---|---|
| 15 | 77 | 23 |
| 30 | 77 | 23 |
| 70 | 92 | 8 |
| collagen reference | 70 | 30 |

The tests indicated the presence of water at all depths. The absolute water concentration appears to stay constant with depth, indicating that it is an integral part of the collagen structure. Carboxyl functionality became significant below 60 Å. Collagen reference material exhibited a similar concentration of carboxyl functionality to that found on the collagen coating at deepest analysis depth, i.e., 70 Å. It is expected that with further increasing analysis depth an intermediate layer consisting of a blend of collagen and poly (acrylic acid) chains will precede the primarily acrylic acid based surface graft matrix.

The described results of the above XPS study are in full agreement with the surface model depicted in FIG. 2. The study demonstrated the presence of a discrete collagen top layer of at least 70 Å thickness. Since at a depth of 60 Å the concentration of carboxyl functionality started to increase progressively, it is expected that with increasing depths the collagen layer will start to lose its integrity and will shift into a blend of collagen and the poly(acrylic acid) making up the surface graft matrix. At some depth in the surface graft matrix, it is expected that substantially no collagen will be found within the surface graft matrix.

In addition to the above described surface analysis techniques, high mass resolution Time-of-Flight Secondary Ion Mass Spectrometry (ToF-SIMS) was also used to investigate the surface of processed collagen-immobilized samples. In ToF-SIMS, a sample surface is bombarded with a primary beam of energetic particles, normally ions. This results in the emission of a range of secondary particles, including positively and negatively charged atomic and molecular species. These secondary ions are subsequently mass analyzed to provide elemental and detailed chemical structure information.

The results of the ToF-SIMS testing also confirmed the presence of a collagen top layer, as the sample spectra displayed a rich array of N-containing signals. In addition to nonspecific peptide/protein characteristics, the spectra exhibit rich arrays of N-containing signals which are more diagnostic of particular amino acid residues. The collagen top layer displayed an outermost surface chemistry which differs to that of the collagen reference. While N-containing species are clearly present, there appears to be a higher relative proportion of species containing C/H and C/H/O for the collagen coating compared to the collagen reference. This indicates either an incomplete collagen top layer or a very thin collagen top layer, or some reorientation of the collagen molecules due to the immobilization.

The overlap between XPS and ToF-SIMS is emphasized by the similar observation that the amino acid residues proline and hydroxyproline are found in increased concentrations at the surface.

Example 3

Evaluation of in vivo Performance of Collagen-Immobilized Samples Collagen-immobilized samples (55D-CC) were prepared as previously described in Example 2 above (100 wt-% acrylic acid monomer used to prepare the surface graft matrix). The in vivo performance was investigated and compared to that of acrylic acid grafted 55D (55D-AA) and plain 55D samples (55D) as discussed below.

Male Albino-Oxford rats (bred at University of Groningen, Groningen, the Netherlands) of approximately three months of age were ether-anaesthetized. The back was shaved and disinfected with 70% ethanol. Six subcutaneous pockets were created to the right and left of three midline incisions. Discs (3 mm diameter) of 55D, 55D-AA, and 55D-CC were implanted in the subcutaneous pockets. Thereafter, the incisions were closed with one suture.

Six rats were used and sacrificed at day 1, 2, 5, 10, and at week 3 and 6 after implantation. At the specific time points the discs were carefully excised with surrounding tissue. All explanted specimens were immersion-fixed in 2% (v/v) glutaraldehyde in PBS (pH 7.4) during at least 24 hours at 4° C. Post-fixation was performed with 1% $OsO_4$ and 1.5% $K_4Fe(CN)_6$ in PBS; subsequently, the specimens were dehydrated in graded alcohols and embedded in EPON 812 (runschwig chemie, Amsterdam, The Netherlands). Prior to light microscopy (LM) evaluation of semithin sections (1 $\mu$m) were prepared and typically stained with Toluidine Blue for one minute, after which the dye was washed off.

The results indicated that 55D-CC induced a more intense tissue response immediately after implantation than 55D and 55D-AA. This resulted in thicker layers of macrophages and granulocytes which could also be observed at day 2 and 5. This intense macrophage/granulocyte reaction apparently is not an immunogenic reaction, since at later time points no significant invasion of lymphocytes in the material-tissue interface was observed.

The initial effect of an increased cellular reaction does not continue indefinitely, i.e., 55D-CC had a similar or thinner tissue capsule compared to 55D and 55D-AA. These results may indicate that 55D-CC promotes a faster wound healing response as a result from its biological interaction with the body's responses. It appears that fibrin formation at the surface of 55D-CC plays a major role, which indicates that 55D-CC may promote coagulation.

Example 4

Covalent Immobilization of Polyethyleneimine (PEI) and Heparin

As discussed above, a majority of the desired biomolecules may be coupled in the outer portion of the primary surface graft matrix through linker molecules covalently coupled to both the surface graft matrix and the biomolecules. Examples of linker molecules useful in connection with the present invention include, e.g., the aminefunctional polymers polyethyleneimine (PEI) or polyallylamine (PALLA). These compounds contain pendant amine-functional groups that can be used to surfaceimmobilize a majority of the biomolecules in the outer portion of a surface graft matrix.

In this example, PEI was surface-immobilized to substantially enclose the surface graft matrix. The PEI was subsequently used to surface-immobilize the anticoagulant drug heparin.

55D PELLETHANE samples were surface grafted with acrylic acid monomer as discussed in Example 1 using 100 wt-% acrylic acid monomer and 70 wt-% acrylic acid monomer with 30 wt-% acrylamide monomer. Subsequently, the surface grafted samples were immersed in a 0.05M tartrate solution (di-sodium tartrate), buffered at pH=3.0 for 30 minutes at room temperature. After a triplicate rinse in DI water, samples were immersed in a solution of 0.1% by weight PEI and 0.01M EDC (pH=4) for 15 minutes.

Surface staining techniques were done to verify whether PEI coupling was successfully performed. Uptake of the anionic dye Ponceau S (PS) is indicative for the presence of PEI. The grafted surface by itself was used as the control. The difference in dye-uptake was obvious visually. To demonstrate that the PEI was covalently coupled, a sample was immersed in 1 wt-% aqueous SDS for 3 days at 60° C.; because of the strong interaction between PEI and SDS, loosely bound PEI will be desorbed from the surface. The control surface had been exposed to PEI in the absence of the coupling reagents EDC and NHS, so that in this case presence of PEI could only be accounted for by simple adsorption. While before SDS-treatment the difference in PS-uptake between the two materials was not that notable; after SDS-treatment the sample with adsorbed PEI did not show any PS uptake anymore. In contrast, the sample with covalently immobilized PEI did not show significant alteration from the original dye uptake.

After the PEI-coupled samples were rinsed in 1 wt-% SDS and DI water to remove adsorbed PEI, coupling of nitrous acid degraded (NAD-)heparin (obtained from CARMEDA, Stockholm, Sweden) was performed. The "PEI-capped" sample was immersed in a 0.2M acetate buffered solution (pH=4.6) of 1 mg/ml NAD-heparin and 1 mM $NaCNBH_3$. The reaction was allowed to proceed for 2 hours at 50° C. Finally, the processed samples were cleaned by a triplicate rinse in 1M NaCl and DI water; samples were dried in air at room temperature.

After heparin coupling, representative samples were stained with the cationic dye Toluidine Blue O (TB). The presence of heparin is denoted by a metachromatic shift from blue to violet. While the primary graft alone demonstrated a blueish, dark violet color after TB-exposure, the heparinized surface demonstrated an obvious shift to light violet. This shift in color suggests successful surface-coupling of heparin. PS-uptake obviously decreased as a consequence of the heparin-coupling; this confirms presence of heparin as well as coupling of heparin reduces the cationic nature of the surface.

SEM analysis confirmed that a majority of the PEI is located within the outer portion of the surface graft matrix. The processed samples were examined by SEM operated at 15 kV; prior to SEM analysis surfaces were sputter-coated with gold. Due to damage of the processed specimen, which may have been caused by a poor drying procedure, several surface faults were induced that revealed a sheath enclosing the primary surface graft matrix. At the surface faults, the structure of the primary surface graft matrix can be well recognized.

Samples were also investigated by means of FT-IR spectroscopy. Heparinization via the PEI-intermediate layer resulted in the appearance of additional peaks in the 1000–1060 $cm^{-2}$ region. These peaks are characteristic of the S—O stretch of the sulfur acid groups, in this case originating from the immobilized heparin molecules. The observed change in the 1530–1730 $cm^{-1}$ region can be assigned to the surface-immobilized PEI; for example, the 1560 $cm^{-1}$ peak is characteristic for N—H (in plane) bend of amides.

Additional surface analysis was performed by XPS. The heparin-immobilized sample exhibited significant heparin concentrations at the graft surface.

The above results demonstrated that active heparin can be coupled to the PEI-sheath; this was confirmed in an in vitro bioassay. Because of their location in the outer layers of the surface graft matrix, it is expected that the immobilized heparin molecules will be more readily accessible and thus exhibit an enhanced bioactivity. This is suggested to be due to the repelling nature of the underlying anionic surface graft matrix, which would prevent penetration of the heparin molecules into the surface graft matrix.

Example 5

Gentamicin Loading of Surface Graft Matrix of PEI/Heparin Coupled Samples

It was demonstrated (Table 12) that the PEI-immobilization and subsequent heparin coupling did not significantly affect the ability of the surface grafted material to load the (polycationic) antimicrobial agent gentamicin. Gentamicin loading was performed by immersion of the samples in a 0.01M MES buffered solution of 0.5 mg/ml gentamicin base (provided as gentamicin sulfate from Sigma Chemie, Bomem, Belguim), adjusted to pH 6.0, by dropwise addition of 1N NaOH, for 30 minutes. After rinsing with DI water, the samples were dried by air exposure at ambient temperature.

The gentamicin solution used for loading the surface grafted sample was analyzed to determine its gentamicin content before and after loading. This was done using a TNBS Assay in which the gentamicin-containing solution was adjusted to pH 9 by addition of 0.1M borate, after which 25 μl 0.03M aqueous TNBS was added per ml of sample-solution. The difference in gentamicin content before and after sample immersion was determined and used as a measure for the amount of gentamicin loaded. The amount of gentamicin loaded was expressed as $\mu g/cm^2$ and is reported below in Table 12.

The gentamicin loading suggests that a majority of the immobilized PEI can be found in the outer portion of the surface graft matrix, i.e., the PEI has formed a relatively thin outer sheath on the matrix. If the PEI was dispersed throughout the surface graft matrix, it would be expected to diminish the capacity of the surface graft matrix to load gentamicin, as it would neutralize much of the negative charge of the surface graft matrix due to penetration of the PEI molecules into the graft matrix.

TABLE 12

Gentamicin loading capacity (mg/cm$^2$) of surface grafted, and surface grafted + heparanized 55D PELLETHANE; effect of graft matrix composition (n = 3).

| sample | grafted sample (PU$_{graft}$) | grafted/heparanized sample (PU$_{hep}$) |
|---|---|---|
| X$_{AA}$ = 1 | 113 ± 24 | 108 ± 14 |
| X$_{AA}$ = 0.7 | 38 ± 7 | 24 ± 5 |

Gentamicin release was performed by immersion of gentamicin loaded samples in phosphate buffered saline (PBS, pH 7.4) at 37° C.; a volume-to-surface ratio of 1:1 (ml:cm$^2$) typically was used throughout the experiment. At desired time points, the samples were withdrawn from the solution and immersed in fresh PBS. Solution samples were analyzed for their gentamicin content by means of the TNBS Assay discussed above.

Heparin coupling did not significantly influence the gentamicin release profile. After an initial burst, gentamicin progressively released until completion in an approximate 2 weeks.

Evaluation of in vitro antibacterial activity of gentamicin loaded samples was evaluated. A strain of *Staphylococcus aureus* (code PW230693), obtained from an actual electrode-associated infection, was used for the antibacterial activity testing. This strain was determined to be gentamicin-sensitive.

Surface grafted, heparinized 55D Pellethane samples were sterilized by exposure to ethylene oxide. The antibacterial activity was determined by a "zone-of-inhibition" test. An isosensitest agar plate (Oxoid Ltd., Hampshire, UK) was seeded with bacteria, for which typically a suspension of ±10$^4$ *S. aureus*/ml saline was used. Subsequently, the test materials were applied (8 mm discs); Genta-neo-sensitab (Rosco Diagnostica, Taastrup, Denmark), a gentamicin-loaded tablet, was used as the positive control. Surface grafted, heparinized samples without gentamicin were applied as negative controls. Subsequently, the agar plate was incubated overnight at 37° C. The following day the plate was removed from the incubator and the bacteria free zone around each sample was determined. The regions of bacterial growth and inhibition are obvious visually.

The results of the antibacterial activity testing is shown in Table 13. After the incubation period a zone-of-inhibition was measured that was approximately 360 mm$^2$ for the grafted, gentamicin loaded sample (PU$_{GS}$) and 350 mm$^2$ for the grafted/heparinized and gentamicin loaded sample (PU$_{hep/GS}$). The non-loaded materials demonstrated no antibacterial activity.

TABLE 13

Antibacterial activity testing of gentamicin-releasing materials; comparison between grafted, and grafted/heparinized surfaces (n = 2).

| Sample | zone-of-inhibition (mm$^2$) |
|---|---|
| grafted (Pu$_{graft}$) | 0 |
| grafted + gentamicin (PU$_{GS}$) | 363 ± 24 |
| grafted/heparinized (PU$_{hep}$) | 0 |
| grafted/heparinized + gentamicin (Pu$_{hep/GS}$) | 347 ± 47 |
| Genta-neo-sensitab control | 617 ± 63 |

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as each were individually incorporated by reference.

What is claimed is:

1. A medical device comprising:
   a) a polymerized surface graft matrix comprising carboxyl-functional groups located on the device, the polymerized surface graft matrix comprising an outer portion; and
   b) one or more biomolecules covalently coupled to the polymerized surface graft matrix, wherein a majority of the biomolecules are located in the outer portion of the polymerized surface graft matrix.

2. A device according to claim 1, wherein a majority of the biomolecules are located within about 10 nm of the outer surface of the polymerized surface graft matrix.

3. A device according to claim 1, wherein the biomolecule is selected from the group consisting of antithrombotic agents, antibacterial agents, anti-inflammatory agents, growth factors, cytokines, naturally occurring or synthetically prepared proteins, peptides, amino acids, and mixtures thereof.

4. A device according to claim 3, wherein the biomolecule is selected from the group consisting of collagen, albumin, fibrinogen, laminin, vitronectin, fibronectin, RGD-containing peptides, heparin, heparin sulfate, fibroblast growth factors (FGF), insulin-like growth factor, nerve growth factor, interferons (IFN), tumor necrosis factors (TNF), interleukins, gelatin, elastin, fibrin, von Willebrand factor, dermatan sulfate, hyaluronic acid, dextran sulfate, and mixtures thereof.

5. A device according to claim 1, wherein the polymerized surface graft matrix is prepared from carboxyl-functional monomers selected from the group consisting of acrylic acid, methacrylic acid, itaconic acid, trans-cinnamic acid, crotonic acid, linoleic acid, linolenic acid, maleic acid, sorbic acid, and mixtures thereof.

6. A device according to claim 1, wherein the polymerized surface graft matrix is prepared from carboxyl-functional monomers and vinyl monomers having no carboxyl functionality.

7. A device according to claim 6, wherein the polymerized surface graft matrix is prepared from acrylic acid monomers and acrylamide monomers.

8. A device according to claim 1, further including a pharmaceutical agent in the polymerized surface graft matrix.

9. A device according to claim 8, wherein the pharmaceutical agent is selected from the group consisting of antimicrobial agents, antibacterial agents, anticoagulant agents, antithrombotic agents, platelet agents, anti-inflammatory agents, dyes which act as biological ligands, steroids, enzymes, catalysts, hormones, growth factors, drugs, vitamins, antibodies, antigens, nucleic acids, peptides, DNA & RNA segments, and mixtures thereof.

10. A medical device comprising:
    a) a polymerized surface graft matrix comprising carboxyl-functional groups located on the device, the polymerized surface graft matrix comprising an outer portion;
    b) one or more linker molecules covalently coupled to the polymerized surface graft matrix, wherein a majority of the linker molecules are located in the outer portion of the polymerized surface graft matrix; and
    c) one or more biomolecules covalently coupled to the linker molecules.

11. A device according to claim 10, wherein a majority of the linker molecules are located within about 10 nm of the outer surface of the polymerized surface graft matrix.

12. A device according to claim 10, wherein the linker molecules, prior to coupling, are amine-functional compounds.

13. A device according to claim 12, wherein the amine-functional compounds are selected from the group consisting of polyethyleneimine, polyallylamine, and mixtures thereof.

14. A device according to claim 10, wherein the biomolecule is selected from the group consisting of antithrombotic agents, antibacterial agents, anti-inflammatory agents, growth factors, cytokines, naturally occurring or synthetically prepared proteins, peptides, and amino acids, and mixtures thereof.

15. A device according to claim 14, wherein the biomolecule is selected from the group consisting of collagen, albumin, fibrinogen, laminin, vitronectin, fibronectin, RGD-containing peptides, heparin, heparin sulfate, fibroblast growth factors (FGF), insulin-like growth factor, nerve growth factor, interferons (IFN), tumor necrosis factors (TNF), interleukins, gelatin, elastin, fibrin, von Willebrand factor, dermatan sulfate, hyaluronic acid, dextran sulfate, and mixtures thereof.

16. A device according to claim 10, wherein the polymerized surface graft matrix is prepared from carboxyl-functional monomers selected from the group consisting of acrylic acid, methacrylic acid, itaconic acid, trans-cinnamic acid, crotonic acid, linoleic acid, linolenic acid, maleic acid, sorbic acid, and mixtures thereof.

17. A device according to claim 10, wherein the polymerized surface graft matrix is prepared from carboxyl-functional monomers and vinyl monomers having no carboxyl functionality.

18. A device according to claim 17, wherein the polymerized surface graft matrix is prepared from acrylic acid monomers and acrylamide monomers.

19. A device according to claim 10, further including a pharmaceutical agent in the polymerized surface graft matrix.

20. A device according to claim 19, wherein the pharmaceutical agent is selected from the group consisting of antimicrobial agents, antibacterial agents, anticoagulant agents, antithrombotic agents, platelet agents, anti-inflammatory agents, dyes which act as biological ligands, steroids, enzymes, catalysts, hormones, growth factors, drugs, vitamins, antibodies, antigens, nucleic acids, peptides, DNA & RNA segments, and mixtures thereof.

* * * * *